United States Patent
Greve (10) Patent No.: US 10,035,836 B1
(45) Date of Patent: Jul. 31, 2018

(54) MODIFIED IL-2 VARIANTS THAT SELECTIVELY ACTIVATE REGULATORY T CELLS

(71) Applicant: DELINIA, INC., Cambridge, MA (US)

(72) Inventor: Jeffrey Greve, Berkeley, CA (US)

(73) Assignee: Delinia, Inc., Emeryville, CA (US)

( * ) Notice: Subject to any disclaimer, the term of this patent is extended or adjusted under 35 U.S.C. 154(b) by 0 days.

(21) Appl. No.: 15/327,813

(22) PCT Filed: Aug. 10, 2015

(86) PCT No.: PCT/US2015/044462
§ 371 (c)(1),
(2) Date: Jan. 20, 2017

(87) PCT Pub. No.: WO2016/025385
PCT Pub. Date: Feb. 18, 2016

Related U.S. Application Data (60) Provisional application No. 62/070,016, filed on Aug. 11, 2014.

(51) Int. Cl.
| | | |
|---|---|---|
| A61K 38/20 | (2006.01) | |
| C07K 14/55 | (2006.01) | |
| A61K 47/48 | (2006.01) | |
| A61K 38/00 | (2006.01) | |

(52) U.S. Cl.
CPC .......... C07K 14/55 (2013.01); A61K 38/2013 (2013.01); A61K 47/48215 (2013.01); A61K 38/00 (2013.01)

(58) Field of Classification Search
CPC ............................ C07K 14/55; A61K 38/2013
See application file for complete search history.

(56) References Cited

U.S. PATENT DOCUMENTS

| | | | |
|---|---|---|---|
| 4,853,332 A | 8/1989 | Mark et al. | |
| 4,902,502 A | 2/1990 | Nitecki et al. | |
| 5,089,261 A | 2/1992 | Nitecki et al. | |
| 5,206,344 A | 4/1993 | Katre et al. | |
| 5,281,698 A | 1/1994 | Nitecki | |
| 5,466,447 A | 11/1995 | Abels et al. | |
| 5,650,150 A | 7/1997 | Gillies | |
| 6,348,192 B1 | 2/2002 | Chan et al. | |
| 6,541,610 B1 | 4/2003 | Smith | |
| 6,602,498 B2 | 8/2003 | Shen | |
| 6,689,353 B1 | 2/2004 | Wang et al. | |
| 6,911,197 B2 | 6/2005 | Shen | |
| 6,927,043 B2 | 8/2005 | Chan et al. | |
| 6,955,807 B1 | 10/2005 | Shanafelt et al. | |
| 7,105,653 B2 | 9/2006 | Shanafelt et al. | |
| 7,148,321 B2 | 12/2006 | Gillies et al. | |
| 7,186,804 B2 | 3/2007 | Gillies et al. | |
| 7,371,371 B2 | 5/2008 | Epstein et al. | |
| 7,452,966 B2 | 11/2008 | Glaesner et al. | |
| 7,462,350 B2 | 12/2008 | Gillies et al. | |
| 7,569,215 B2 | 8/2009 | Wittrup et al. | |
| 7,579,439 B2 | 8/2009 | Strom et al. | |
| 7,888,071 B2 | 2/2011 | Gillies et al. | |
| 7,951,360 B2 | 5/2011 | Wittrup et al. | |
| 8,012,465 B2 | 9/2011 | Elias et al. | |
| 8,043,608 B2 | 10/2011 | Gillies et al. | |
| 8,066,994 B2 | 11/2011 | Gillies et al. | |
| 8,124,066 B2 | 2/2012 | Epstein et al. | |
| 8,349,311 B2 | 1/2013 | Wittrup et al. | |
| 8,454,946 B2 | 6/2013 | Shen et al. | |
| 8,765,111 B2 | 7/2014 | Shen | |
| 8,992,902 B2 | 3/2015 | Shen | |
| 8,993,524 B2 | 3/2015 | Bedi et al. | |
| 9,169,350 B2 | 10/2015 | Shen | |
| 9,206,243 B2 | 12/2015 | León et al. | |
| 9,289,493 B2 | 3/2016 | Ko | |
| 2004/0171154 A1 | 9/2004 | Storici et al. | |
| 2006/0160187 A1 | 7/2006 | Denis-Mize et al. | |
| 2007/0036752 A1 | 2/2007 | Gillies et al. | |
| 2011/0020266 A1 | 1/2011 | Nissen et al. | |
| 2011/0091412 A1 | 4/2011 | Wittrup et al. | |
| 2011/0150826 A1 | 6/2011 | Paulsen et al. | |
| 2011/0274650 A1 | 11/2011 | Gavin et al. | |
| 2012/0276125 A1 | 11/2012 | Ast et al. | |
| 2013/0195795 A1 | 8/2013 | Gavin et al. | |
| 2014/0004080 A1 | 1/2014 | Klatzmann et al. | |
| 2014/0044675 A1 | 2/2014 | Hosse et al. | |
| 2014/0046026 A1 | 2/2014 | Garcia et al. | |

(Continued)

FOREIGN PATENT DOCUMENTS

| | | |
|---|---|---|
| CN | 102174111 A | 9/2011 |
| CN | 103193887 A | 7/2013 |

(Continued)

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990), pp. 126-128 and 228-234.*
Bensinger et al. "Distinct IL-2 Receptor Signaling Pattern in CD4$^+$CD25$^+$ Regulatory T Cells[1] ", 2004, J Immunol. 172(9): 5287-5296.
Hoffmann et al., " Donor-type CD4$^{+CD25+}$ Regulatory T Cells Suppress Lethal Acute Graft-Versus-Host Disease after Allogeneic Bone Marrow Transplantation", 2002, J. Exp. Med. 196(3): 389-399.
Sykes, et al., In Vivo Administration of Interleukin 2 Plus T Cell-Depleted Syngeneic Marrow Prevents Graft-Versus-Host Disease Mortality and Permits Alloengraftment, The Journal of Experimental Medicine, vol. 171 Mar. 1990 pp. 645-658.

(Continued)

*Primary Examiner* — Prema Mertz
(74) *Attorney, Agent, or Firm* — McCarter & English, LLP (57) ABSTRACT

The invention described herein is a novel IL-2 protein with selective agonist activity for Regulatory T cells and with an additional amino acid substitution that enable chemical conjugation with Polyethyene Glycol (PEG) that increase circulating half-life compared to the IL-2 selective agonist alone. A preferred IL-2 selective agonist variant is IL2/N88R/C125S/D109C.

5 Claims, 6 Drawing Sheets

(56) References Cited

U.S. PATENT DOCUMENTS

| | | | |
|---|---|---|---|
| 2014/0285898 | A1 | 9/2014 | Moliton |
| 2014/0286898 | A1 | 9/2014 | Gavin et al. |
| 2014/0328791 | A1 | 11/2014 | Bossard et al. |
| 2014/0343252 | A1 | 11/2014 | Gavin et al. |
| 2015/0017120 | A1 | 1/2015 | Wittrup et al. |
| 2015/0132254 | A1 | 5/2015 | Wittrup et al. |
| 2015/0218260 | A1 | 8/2015 | Klein et al. |
| 2015/0335669 | A1 | 11/2015 | Chae et al. |
| 2015/0374788 | A1 | 12/2015 | Paulsen et al. |
| 2016/0083514 | A1 | 3/2016 | Shen |
| 2016/0090407 | A1 | 3/2016 | Hosse et al. |
| 2016/0208017 | A1 | 7/2016 | Ast et al. |
| 2016/0263240 | A1 | 9/2016 | Ast et al. |

FOREIGN PATENT DOCUMENTS

| | | | |
|---|---|---|---|
| EP | 1370280 | A2 | 12/2003 |
| EP | 1076704 | B1 | 1/2007 |
| EP | 1454138 | A4 | 2/2007 |
| EP | 1688146 | B1 | 7/2007 |
| EP | 2288372 | B1 | 2/2012 |
| WO | WO 90/00565 | * | 1/1990 |
| WO | WO-1995-008340 | | 3/1995 |
| WO | WO-1999-043713 | | 9/1999 |
| WO | WO-1999-060128 | | 11/1999 |
| WO | WO-2005-014642 | A2 | 2/2005 |
| WO | WO-2010-085495 | A1 | 7/2010 |
| WO | WO-2011109789 | A2 | 9/2011 |
| WO | WO-2012107417 | A1 | 8/2012 |
| WO | WO-2012-146628 | A1 | 11/2012 |
| WO | WO-2014023752 | A1 | 2/2014 |
| WO | WO-2014145907 | A1 | 9/2014 |
| WO | WO-2014-201378 | A1 | 12/2014 |
| WO | WO-2015-164815 | A1 | 10/2015 |
| WO | WO-2016014428 | A2 | 1/2016 |
| WO | WO-2016-025645 | A1 | 2/2016 |
| WO | WO-2016-025647 | A1 | 2/2016 |
| WO | WO-2016025385 | A1 | 2/2016 |
| WO | WO-2016-057651 | A1 | 4/2016 |

OTHER PUBLICATIONS

Sykes, et al., Interleukin 2 prevents graft-versus-host disease while preserving the graft-versus-leukemia effect of allogeneic T cells, Proceedings of the National Academy of Sciences, Aug. 1990, vol. 87, pp. 5633-5637.
Zorn et al., IL-2 regulates FOXP3 expression in human CD4+CD25+ regulatory T cells through a STAT-dependent mechanism and induces the expansion of these cells in vivo, Blood, Sep. 1, 2006, vol. 108, No. 5, pp. 1571-1579.
Zorn, et al., Combined CD4+ Donor Lymphocyte Infusion and Low-Dose Recombinant IL-2 Expand FOXP3+ Regulatory T Cells following Allogeneic Hematopoietic Stem Cell Transplantation, Biol Blood Marrow Transplant, Mar. 2009, 15(3), pp. 382-388.
Altschul, et al., Basic local alignment search tool., Oct. 1990, J. Mol. Biol. 215:403-410, doi:10.1016/S0022-2836(05)80360-2.
Altschul et al., Gapped BLAST and PSI-BLAST: a new generation of protein database search programs., Nucleic Acids Res., 1997 25(17):3389-3402.
Argos, An investigation of oligopeptides linking domains in protein tertiary structures and possible candidates for general gene fusion., 1990, J Mol. Biol. 211:943-58, doi:10.1016/0022-2836(90)90085-Z.
Atkins, et al., Hypothyroidism after treatment with interleukin-2 and lymphokine-activated killer cells, N Engl. J. Med, Jun. 16, 1988, 318(24):1557-63.
Batzer, et al., Enhanced evolutionary PCR using oligonucleotides with inosine at the 3'-terminus, Nucleic Acid Res., 1991, 19:5081.
Bell, et al., Sustained in vivo signaling by long-lived IL-2 induces prolonged increases of regulatory T cells., J Autoimmunity, Jan. 2015, 56:66-80.

Calissano, et al., In vivo site-directed mutagenesis of Neurospora crassa beta-tubulin gene by spheroplasts transformation with oligonucleotides,1996, Fungal Genet. Newsletter 43: 15-16.
Cantrell, et. al, The interleukin-2 T-cell system: a new cell growth model Jun. 22, 1984, Science, 224:1312-1316, DOI: 10.1126/science.6427923.
Cassell, et. al., Therapeutic Enhancement of IL-2 Through Molecular Design, 2002, Curr Pharm Des., 8:2171-83.
Chen, et al., IL-2 Controls the Stability of Foxp3 Expression in TGF-β-Induced Foxp3+ T Cells In Vivo, 2011, J Immunol, 186:6329-37.
Chen et al., Fusion protein linkers: Property, design and functionality., Adv. Drug Delivery Rev.., Oct. 2013, 65(10):1357-69.
Chianese-Bullock, et al., Autoimmune toxicities associated with the administration of antitumor vaccines and low-dose interleukin-2, J Immunother, Jul.-Aug. 2005, 28(4):412-9.
Co-pending U.S. Appl. No. 15/002,144, filed Jan. 20, 2016.
Co-pending U.S. Appl. No. 15/265,764, filed Sep. 14, 2016.
Co-pending U.S. Appl. No. 15/265,770, filed Sep. 14, 2016.
Czajkowsky, et al., Fc-fusion proteins: new developments and future perspectives., 2012; EMBO Mol Med. 4(10):1015-28 DOI 10.1002/emmm.201201379.
Dauphinee, et al., Interleukin 2 deficiency is a common feature of autoimmune mice, J Immunology, Dec. 1981,127(6):2483-7.
Davey et al., Safety, Tolerability, Pharmacokinetics, and Efficacy of an Interleukin-2 Agonist Among HIV-Infected Patients Receiving Highly Active Antiretroviral Therapy., Feb. 16, 2008, J Cytokine Res. 28(2): 89-100. doi:10.1089/jir.2007.0064.
Dunmont et, al., Impact on Pharmacokinetic and Biological Activity of Protein Therapeutics., May 2006, BioDrugs 20(3)151-60 DOI: 10.2165/00063030-200620030-00002.
Furtado, et al., Interleukin 2 signaling is required for CD4+ regulatory T cell function, JEM, Sep. 16, 2002,196(6): 851-857.
Gillies, et al., Antibody-targeted interleukin 2 stimulates T-cell killing of autologous tumor cells., Immunology, Feb. 1992, Proc Natl Acad Sci, 89:1428-32.
Gillies et al., Improved Circulating Half-Life and Efficacy of an Antibody-Interleukin 2 Immunocytokine Based on Reduced Intracellular Proteolysis., Jan. 2002, Clinical Cancer Res., 8:210-6.
Hecht, et al., Rationale-Based Engineering of a Potent Long-Acting FGF21 Analog for the Treatment of Type 2 Diabetes., PLOS One. 7(11):e49345, Published: Nov. 27, 2012 • http://dx.doi.org/10.1371/journal.pone.0049345.
Huanget, et al., Restoration of an early, progressive defect in responsiveness to T-cell activation in lupus mice by exogenous IL-2, Autoimmunity, 1993;15(1):19-29.
International Search Report dated Jan. 29, 2016 for PCT-US15-041177.
International Search Report dated Dec. 8, 2015 for PCT/US2015/044462.
Jailwala, et al., Apoptosis of CD4+CD25 high T Cells in Type 1 Diabetes May Be Partially Mediated by IL-2 Deprivation, Aug. 2009, PLOS One. 2009; 4:e6527, 1-13.
Karlin, et al., Methods for assessing the statistical significance of molecular sequence features by using general scoring schemes, Proc. Natl. Acad. Sci. USA, 1990, 87:22264•2268.
King et al., Phase I Clinical Trial of the Immunocytokine EMD 273063 in Melanoma Patients., J. Clinical Oncology, Nov. 15, 2004, 22:4463-73.
Kirchner, et al., Pharmacokinetics of recombinant human interleukin-2 in advanced renal cell carcinoma patients following subcutaneous application., Jul. 1998, 46:5-10, 10.1046/j.1365-2125.1998.00036.x.
Kitas, et al., Deficient interleukin 2 production in rheumatoid arthritis,association with active disease and systemic complications, Bacon PA. Clin Exp Immunol. Aug. 1988;73(2):242-9.
Klatzmann, et al., The promise of low-dose interleukin-2 therapy for autoimmune and inflammatory diseases., Apr. 17, 2015, Nat Rev Immunol, 15:283-94.
Koreth, et al., Interleukin-2 and Regulatory T Cells in Graft-versus-Host Disease., Dec. 1, 2011, New Engl. J Med., 365(2):2055-66.

(56) References Cited

OTHER PUBLICATIONS

Kren et al., In vivo site-directed mutagenesis of the factor IX gene by chimeric RNA/DNA oligonucleotides., Nat Med. Nature Med 4, 1998 285-290 doi:10.1038/nm0398-285.
Kroemer et al., The role of interleukin 2 in autoimmunity, Immunol Today, Jul. 1989, 10(7):246-51.
Liston, et. al., Tracing the action of IL-2 in tolerance to islet-specific antigen, Immunology and Cell Biology (2007) 85, 338-342.
Liu, et al., A Novel Antibody Engineering Strategy for Making Monovalent Bispecific Heterodimeric IgG Antibodies by Electrostatic Steering Mechanism, J Biol Chem., Mar. 20, 2015, 290:7535-62.
Long, et al., Defects in IL-2R Signaling Contribute to Diminished Maintenance of FOXP3 Expression in CD4 CD25 Regulatory T-Cells of Type 1 Diabetic Subjects., Feb. 2010, Diabetes 59:407-15.
Mahmud, et al., Interleukin-2 and STAT5 in regulatory T cell development and function, JAK-STAT, Published online: Jan. 1, 2013, 2:1, e23154, 1-7.
Malek, et al., CD4 regulatory T cells prevent lethal autoimmunity in IL-2Rbeta-deficient mice: Implications for the nonredundant function of IL-2, Immunity, Aug. 2002, 17(2):167-78.
Malek, et al., Interleukin-2 Receptor Signaling: At the Interface between Tolerance and Immunity, 2010, Immunity, 33: 153-65.
Malek, et al., Tolerance, not immunity, crucially depends on IL-2, Nat Rev Immunol. Sep. 2004, 4(9):665-74.
Margolin, et al., Phase I Trial of BAY 50-4798, an Interleukin-2/\Specific Agonist in Advanced Melanoma and Renal Cancer, Clin Cancer Res., Jun. 1, 2007, 13:3312-9.
Moschos, et al., Focus on FOCIS: interleukin 2 treatment associated autoimmunity, Clin Immunol, May 2008,127(2):123-9. doi: 10.1016/j.clim.2008.02.011.
Myszka, et al., Kinetic analysis of ligand binding to interleukin-2 receptor complexes created on an optical biosensor surface, Protein Sci, 1996, 5:2468-78.
Oganesyan, et al., 2008, Structural characterization of a human Fc fragment., Acta Crystallogr D (2008), Biol Crystallography, 64:700-704 doi:10.1107/S0907444908007877.
Ohtsuka, et al., An alternative approach to deoxyoligonucleotides as hybridization probes by insertion of deoxyinosine at ambiguous codon positions, Mar. 10, 1985, J. Biol. Chem. 260:2605-208.
Penichet, et al., Antibody-IL-2 fusion proteins: A novel strategy for immune potentiation., J Human Antibodies, 1997 8(1):106-118.
Poli, et al., CD56 bright natural killer (NK) cells: an important NK cell subset, Immunology 2009, 126, 458-465.
Prometheus Laboratories Inc., PROLEUKIN® (aldesleukin) for intravenous infusion. Available at http://www.prouleuldn.com/assets/pdf/proleukin.pdf. Accessed on Oct. 11, 2016.
Rabinovitch, et al., Combination therapy with sirolimus and interleukin-2 prevents spontaneous and recurrent autoimmune diabetes in NOD mice, Diabetes, Mar. 2002, 51(3):638-45.
Ribas et al., Phase I/II open-label study of the biologic effects of the interleukin-2 immunocytokine EMD 273063 (hu14.18-IL2) in patients with metastatic malignant melanoma., J Transl Med., Jul. 29, 2009 7:68.
Ring, et al., Mechanistic and structural insight into the functional dichotomy between IL-2 and IL-15., Oct. 28, 2012, Nat Immunol. 13:1187-95, doi:10.1038/ni.2449.
Rossolini, et al., Use of deoxyinosine-containing primers vs degenerate primers for polymerase chain reaction based on ambiguous sequence information., Apr. 1994, Mol. Cell. Probes 8:91-98.
Saadoum, et al., Regulatory T-Cell Responses to Low-Dose Interleukin-2 in HCV-Induced Vasculitis., New Engl. Journal of Med., Dec. 1, 2011, 365:2067-77.
Sadlack, et al., Generalized autoimmune disease in interleukin-2-deficient mice is triggered by an uncontrolled activation and proliferation of CD4+ T cells, Eur. J Immunology, Nov. 1995, 25(11):3053-9.
Salfeld, Isotype selection in antibody engineering, Nature Biotechnology, Dec. 2007, 25:1369-72.
Schellenberger, et. al., A recombinant polypeptide extends the in vivo half-life of peptides and proteins in a tunable manner., Nov. 15, 2009, Nat Biot. 27:1186-90.
Schlapschy, et al., Fusion of a recombinant antibody fragment with a homo-amino-acid polymer: effects on biophysical properties and prolonged plasma half-life Jun. 26, 2007, Protein Eng. Des Sel. 20:273-84.
Serreze, et al., Immunostimulation circumvents diabetes in NOD/Lt mice, 1989, J. Autoimmunity, 2:759-776, doi:10.1016/0896-8411(89)90003-6.
Shanafelt, et al., A T-cell-selective interleukin 2 mutein exhibits potent antitumor activity and is well tolerated in vivo., 2000, Nat Biot 18:1197-202 doi:10.1038/81199.
Sleep, et al., Albumin as a versatile platform for drug half-life extension, Biochim Biophys Acta, 2013, 1830:5526-34.
Sondel et al., Current and Potential Uses of Immunocytokines as Cancer Immunotherapy., Antibodies 2012 1 149-171; doi:10.3390/antib1020149.
Steppan, et al., Genome Wide Expression Profiling of Human Peripheral Blood Mononuclear Cells Stimulated With BAY 50/4798, a Novel T Cell Selective Interleukin-2 Analog, J Immunother, Feb./Mar. 2007, 30(2)150-168.
Steppan, et al., Reduced Secondary Cytokine Induction by BAY 50-4798, a High-Affinity Receptor-Specific Interleukin-2 Analog, Journal of Interferon & Cytokine Research, 2006, 26:171-178.
Storici, et al., In vivo site-directed mutagenesis using oligonucleotides, Nature Biotechnology, 2001, 19: 773-776.
Suzuki, et al., Deregulated T cell activation and autoimmunity in mice lacking interleukin-2 receptor beta, Science, Jun. 9, 1995, 268(5216):1472-6.
Tang, et al., Central role of defective interleukin-2 production in the triggering of islet autoimmune destruction, Immunity, 28:687-697. doi:10.1016/ (2008).
Tang, et al., In vitro-expanded antigen-specific regulatory T cells suppress autoimmune diabetes, J. Exp. Med, Jun. 7, 2004, 199(11):1455-65.
Tang, Q., et al, Regulatory T-Cell Therapy in Transplantation: Moving to the Clinic., 2013, Cold Spring Harb. Perspect. Med., 3: 1-15.
Tao et al., Studies of aglycosylated chimeric mouse-human IgG. Role of carbohydrate in the structure and effector functions mediated by the human IgG constant region., J Immunology, Oct. 15, 1989,143(8):2595-2601.
Tian, et al, Accurate multiplex gene synthesis from programmable DNA microchips., Nature 432:1050-1054 doi:10.1038/nature03151.
Wang, et al., Structure of the Quaternary Complex of Interleukin-2 with Its α, β, and γc Receptors., Nov. 18, 2005, Sci. 310:1159-63, DOI: 10.1126/science.1117893.
Weishaupt, et al., The T cell-selective IL-2 mutant AlC284 mediates protection in a rat model of Multiple Sclerosis, J. Neuroimmunol, May 15, 2015, 282:63-72.
Willerford, et al., Interleukin-2 receptor alpha chain regulates the size and content of the peripheral lymphoid compartment, Immunity, Oct. 1995, 3(4):521-30.
You, et al., Adaptive TGf-beta-dependent regulatory T cells control autoimmune diabetes and are a privileged target of anti-CD3 antibody treatment, Proc Natl Acad Sci, Apr. 10, 2007, 104(15):6335-40.
Zheng, et al., Favorably Tipping the Balance between Cytopathic and Regulatory T Cells to Create Transplantation Tolerance., J Immunity, Oct. 2003 19(4):503-514.
Zheng, et al., IL-2 Receptor-Targeted Cytolytic IL-2/Fc Fusion Protein Treatment Blocks Diabetogenic Autoimmunity in Nonobese Diabetic Mice, J Immunol, 1999, 163:4041-8.
Zhu et al., Remodeling domain interfaces to enhance heterodimer formation., Protein Science (1997), 6781-788.
Zhu, et el., Synergistic Innate and Adaptive Immune Response to Combination Immunotherapy with Anti-Tumor Antigen Antibodies and Extended Serum Half-Life IL-2, Cancer Cell, 2015, 13:27(4):489-501.
U.S. Appl. No. 15/265,764, filed Sep. 14, 2016, US 2017/0037102, Abandoned.

(56) References Cited

OTHER PUBLICATIONS

U.S. Appl. No. 15/265,770, filed Sep. 14, 2016, US 2017/0051029, Abandoned.
U.S. Appl. No. 15/662,633, filed Jul. 28, 2017, Pending.
U.S. Appl. No. 15/002,144, filed Jan. 20, 2016, US 2017/0204154, Pending.
Supplementary European Search Report based on co-pending European Patent Application No. 15831523.4, dated Dec. 1, 2017—5 Pages.
Chen, Sharon A. et al., "Plasma and Lymph Pharmacokinectics of Recombinant Human Interleukin-2 and Polyethylene Glycol-Modified Interleukin-2 in Pigs", Apr. 2000, Journal of Pharmacology and Experimental Therapeutics, vol. 293, No. 1, pp. 248-259.
Katre, Nandini V., et al., "Chemical Modification of Recombinant Interleukin 2 by Polyethylene Glycol Increases its Potency in the Murine Meth A Sarcoma Model", Mar. 1987, Proceedings National Academy of Sciences PNAS. vol. 84, No. 6, pp. 1487-1491.

\* cited by examiner

SEQUENCE LISTING

<160> NUMBER OF SEQ ID NOS: 1

<210> SEQ ID NO 1
<211> LENGTH: 133
<212> TYPE: PRT
<213> ORGANISM: Homo sapiens

<400> SEQUENCE: 1

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
            130
```

MODIFIED IL-2 VARIANTS THAT SELECTIVELY ACTIVATE REGULATORY T CELLS

CROSS-REFERENCES TO RELATED APPLICATIONS

This application claims the benefit of priority to U.S. Provisional Patent Application No. 62/070,016, filed on Aug. 11, 2014, the content of which is hereby incorporated by reference.

SUBMISSION OF SEQUENCE LISTING

The Sequence Listing associated with this application is filed in electronic format via EFS-Web and hereby is incorporated by reference into the specification. The name of the text file containing the Sequence Listing is 127754_00202_Sequence_Listing. The size of the text file is 2 KB, and the text file was created on Jun. 27, 2017.

BACKGROUND OF THE INVENTION

The immune system must be able to discriminate between self and non-self. When self/non-self discrimination fails, the immune system destroys cells and tissues of the body and as a result causes autoimmune diseases. Regulatory T cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, has been largely unsuccessful.

Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function. Consequently, there is great interest in the development of therapies that boost the numbers and/or function of Treg cells.

One treatment approach for autoimmune diseases being investigated is the transplantation of autologous, ex vivo-expanded Treg cells (Tang, Q., et al, 2013. Cold Spring Harb. Perspect. Med., 3:1-15). While this approach has shown promise in treating animal models of disease and in several early stage human clinical trials, it requires personalized treatment with the patient's own T cells, is invasive, and is technically complex. Another approach is treatment with low dose Interleukin-2 (IL-2). Treg cells characteristically express high constitutive levels of the high affinity IL-2 receptor, IL2Rαβγ, which is composed of the subunits IL2RA (CD25), IL2RB (CD122), and IL2RG (CD132), and Treg cell growth has been shown to be dependent on IL-2 (Malek, T. R., et al., 2010, Immunity, 33:153-65). Clinical trials of low-dose IL-2 treatment of chronic GVHD (Koreth, J., et al., 2011, N Engl J Med., 365:2055-66) and HCV-associated autoimmune vasculitis patients (Saadoun, D., et al., 2011, N Engl J Med., 365:2067-77) have demonstrated increased Treg levels and signs of clinical efficacy. New clinical trials investigating the efficacy of IL-2 in multiple other autoimmune and inflammatory diseases have been initiated.

Proleukin (marketed by Prometheus Laboratories, San Diego, Calif.), the recombinant form of IL-2 used in these trials, is associated with high toxicity. Proleukin is approved for the treatment of Metastatic Melanoma and Metastatic Renal Cancer, but its side effects are so severe that its use is only recommended in a hospital setting with access to intensive care (Web address: www.proleukin.com/assets/pdf/proleukin.pdf). Until the more recent characterization of Treg cells, IL-2 was considered to be an immune system stimulator, activating T cells and other immune cells to eliminate cancer cells. The clinical trials of IL-2 in autoimmune diseases have employed lower doses of IL-2 in order to target Treg cells, because Treg cells respond to lower concentrations of IL-2 than many other immune cell types due to their expression of IL2Rαβγ (Klatzmann D, 2015 Nat Rev Immunol. 15:283-94). However, even these lower doses resulted in safety and tolerability issues, and the treatments used have employed daily subcutaneous injections, either chronically or in intermittent 5 day treatment courses. Therefore, there is a need for an autoimmune disease therapy that potentiates Treg cell numbers and function, that targets Treg cells more specifically than IL-2, that is safer and more tolerable, and that is administered less frequently.

One approach to improving the therapeutic index of IL-2-based therapy is to use variants of IL-2 that are selective for Treg cells relative to other immune cells. IL-2 receptors are expressed on a variety of different immune cell types, including T cells, NK cells, eosinophils, and monocytes, and this broad expression pattern likely contributes to its pleiotropic effect on the immune system and high systemic toxicity. The IL-2 receptor exists in three forms: (1) the low affinity receptor, IL2RA, which does not signal; (2) the intermediate affinity receptor (IL2Rβγ), composed of IL2RB and IL2RG, which is broadly expressed on conventional T cells (Tcons), NK cells, eosinophils, and monocytes; and (3) the high affinity receptor (IL2Rαβγ), composed of IL2RA, IL2RB, and IL2RG, which is expressed transiently on activated T cells and constitutively on Treg cells. IL-2 variants have been developed that are selective for IL2Rαβγ relative to IL2Rβγ (Shanafelt, A. B., et al., 2000, Nat Biotechnol. 18:1197-202; Cassell, D. J., et. al., 2002, Curr Pharm Des., 8:2171-83). These variants have amino acid substitutions which reduce their affinity for IL2RB. Because IL-2 has undetectable affinity for IL2RG, these variants consequently have reduced affinity for the IL2Rβγ receptor complex and reduced ability to activate IL2Rβγ-expressing cells, but retain the ability to bind IL2RA and the ability to bind and activate the IL2Rαβγ receptor complex. One of these variants, IL2/N88R (Bay 50-4798), was clinically tested as a low-toxicity version of IL-2 as an immune system stimulator, based on the hypothesis that IL2Rβγ-expressing NK cells are a major contributor to toxicity. Bay 50-4798 was shown to selectively stimulate the proliferation of activated T cells relative to NK cells, and was evaluated in phase I/II clinical trials in cancer patients (Margolin. K., et. al., 2007, Clin Cancer Res., 13:3312-9) and HIV patients (Davey, R. T., et. al., 2008, J Interferon Cytokine Res., 28:89-100). These clinical trials showed that Bay 50-4798 was considerably safer and more tolerable than Proleukin, and also showed that it increased the levels of CD4+CD25+ T cells, a cell population enriched in Treg cells. Subsequent to these trials, research in the field more fully established the identity of Treg cells and demonstrated that Treg cells selectively express IL2Rαβγ (reviewed in Malek, T. R., et al., 2010, Immunity, 33:153-65). Based on this new research, it can now be understood that IL2Rαβγ selective agonists should be selective for Treg cells.

Figure 1:
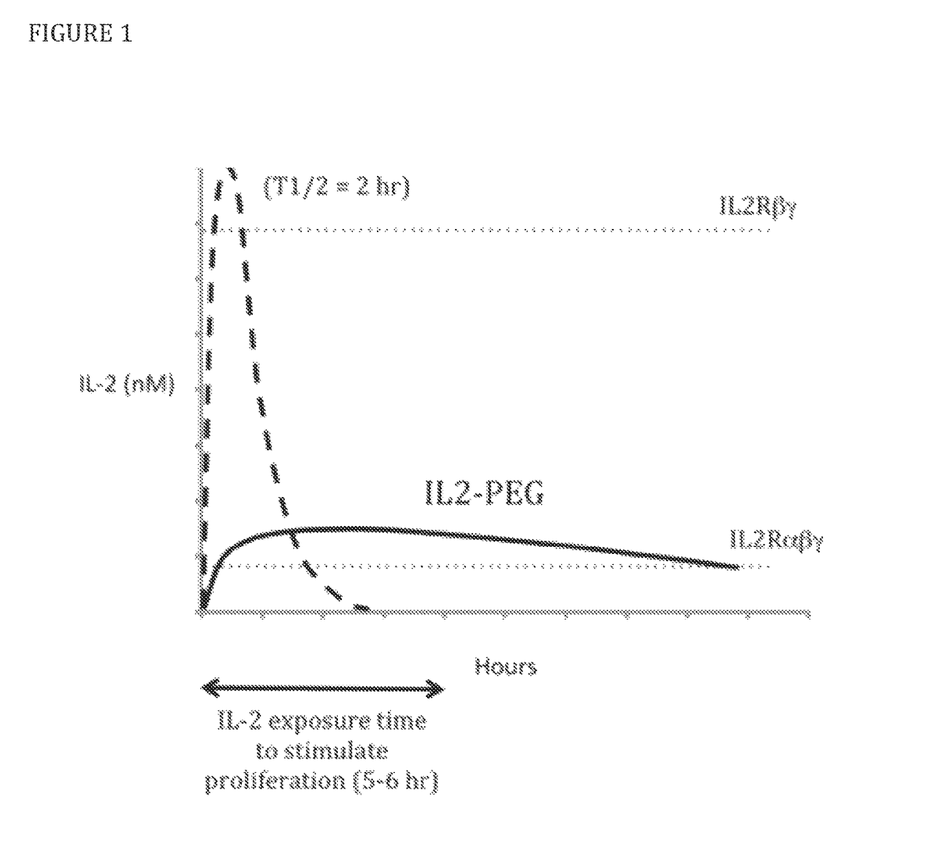
FIG. 1 is a diagrammatic illustration of the relationship between circulating half-life, peak drug level, the biological effective concentration, and the duration necessary to stimulate Treg cell proliferation after a single dose of IL-2 or an IL-2-PEG protein with increased half-life. The dashed line represents the blood level over time of IL-2 following a subcutaneous injection, and the solid line represents the blood level over time of an IL2-PEG conjugate. The horizontal dotted lines indicate the concentrations (EC50 values) necessary to activate cells expressing IL2Rαβγ and IL2Rβγ, respectively) are indicated. The double-headed arrow indicates the duration of exposure (5-6 hr) to IL-2 at the EC50 necessary to stimulate cell proliferation.

A second approach to improving the therapeutic index of an IL-2 based therapy is to optimize the pharmacokinetics of the molecule to maximally stimulate Treg cells. Early studies of IL-2 action demonstrated that IL-2 stimulation of human T cell proliferation in vitro required a minimum of 5-6 hours exposure to effective concentrations of IL-2 (Cantrell, D. A., et. al., 1984, Science, 224: 1312-1316). When administered to human patients, IL-2 has a very short plasma half-life of 85 minutes for intravenous administration and 3.3 hours subcutaneous administration (Kirchner, G. I., et al., 1998, Br J Clin Pharmacol. 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration (FIG. 1). These high IL-2 peak levels can activate IL2Rβγ receptors and have other unintended or adverse effects. An IL-2 analog with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Less frequent subcutaneous administration of an IL-2 drug will also be more tolerable for patients. A therapeutic with these characteristics will translate clinically into improved pharmacological efficacy, reduced toxicity, and improved patient compliance with therapy.

One approach to extending the half-life of therapeutic proteins is to conjugate the therapeutic protein with a non-immunogenic water-soluble polymer like polyethylene glycol (PEG). Chemical conjugation of a protein to a PEG molecule (PEGylation) increases the circulating half-life by increasing the effective hydrodynamic radius of the protein, thus reducing the rate at which the protein conjugate is filtered out of blood by the kidney. IL-2 and IL-2 Selective Agonists are relatively small proteins of approximately 15,000 daltons (15 kDa) with a rapid rate of renal clearance. The circulating half-life of PEG molecules increases in proportion to the molecular weight of the PEG (Yamaoka, T., et al., 1994 J Pharm Sci. 83:601-6).

There are a number of factors which impact the successful production and manufacturing of PEGylated therapeutic proteins. First, because PEGylated proteins are prepared by chemical conjugation of a PEG molecule and a protein, it is important that the protein can be manufactured efficiently because of the additional manufacturing steps involved with PEGylation. Second, the PEG moiety should be should be efficiently conjugated to the protein via a specific amino acid residue, leading to a homogeneous product with high yield. Third, the site of PEGylation on the protein should be chosen so as to minimally interfere with the therapeutic activity of the protein. Interference with the protein therapeutic activity could be due to conjugation of the PEG to the active site of the protein, or could be due to steric hinderance of the active site by the PEG. As an example, one form of PEGylated IL-2 was previously reported in which PEG molecules were conjugated to primary amines on IL-2, resulting in a heterogenous mixture of protein species containing between one and four PEG polymers per IL-2 molecule (Katre, N. V. et. al., 1987 *Proc Natl Acad Sci USA.* 84:1487-91; Knauf, M. J., et. al., 1988 J Biol Chem. 15; 263:15064-701988) which exhibited 4-6 fold reduced biological activity relative to IL-2 (Chen, S. A., 2000 *J.* *Pharmacol Exp Ther.* 293:248-59). Because the IL-2 Selective Agonist must bind and activate to a complex of three receptor subunits on Treg cells, the appropriate conjugation site on IL-2 must be chosen carefully for optimal bioactivity.

This invention concerns variants of IL-2 with single amino acid substitutions at specific positions in the IL-2 sequence that enable stable and specific chemical conjugation of PEG molecules while retaining the ability of the IL-2-PEG conjugate to activate Treg cells. These specified amino acid positions, defined as PEG conjugation sites, are chosen such that the IL-2-PEG conjugate resulting from conjugation of a PEG molecule to IL-2 variant is minimally impaired in its ability to bind to and activate the IL2Rαβγ receptor. This invention also concerns IL-2 variants with aforementioned PEG conjugation sites on IL-2 variants that are selective for the IL2Rαβγ receptor, and consequently have high selectivity for Treg cells.

Chemically activated PEGs have been developed with a number of different chemically reactive groups for conjugation to proteins, enabling conjugation to amino acid residues containing primary amines or to thiol groups. Of these, thiol groups, uniquely present on cysteine residues, enable the most selective conjugation of PEGs to proteins, and PEGs with maleimide or iodoacetamide reactive groups react very selectively with free cysteine thiols. Most cysteine residues in extracellular proteins participate in disulfide bonds that stabilize the protein conformation, and the small number of free (unpaired) cysteine residues are usually buried in the interior of proteins (Petersen, M. T., et. al., 1999 Protein Eng. 1999 12:535-48). PEG conjugation to free cysteine residues in a protein requires either a natural exposed free cysteine residue or the introduction of a novel free cysteine residues. The engineering of a novel free cysteine into a protein carries the risk that the introduced novel cysteine can form an inappropriate intrachain disulfide bond with other cysteines, thus causing misfolding of the protein, or can form interchain disulfide bonds with other molecules, thus causing protein aggregation. IL-2 variants with mutated cysteine residues can exhibit substantially reduced activity due to mispaired disulfide bonds (Wang, A., et al., 1984 Science. 224:1431-3). The invention herein focuses on the engineering of novel, free cysteine residues into IL-2 variant proteins that will be compatible with proper protein folding, that enables site-specific conjugation of a thiol-reactive PEG, and results in an IL-2-PEG conjugate that retains the ability to bind to and activate the IL2Rαβγ on Tregs.

BRIEF DESCRIPTION OF THE DRAWINGS

FIG. 4 shows the selective activation of pSTAT5 by IL2/N88R/C125S/D109C and PEGylated IL2/N88R/C125S/D109C in a T cell subpopulation enriched for Treg cells. Human PBMC were incubated with the samples indicated on the top of each plot for 10 minutes at 37 C. fixed, permeabilized, stained with antibodies, and then subjected to flow cytometry. FACS plots are displayed in pseudocolor mode. Cells gated as CD4+ are shown, and cells were further gated as shown in each of the 4 quadrants. The numbers in each quadrant indicate the percentage of CD4+ cells in each gate. Cells in the upper quadrants represent the highest 1-2% of CD25 expressing cells, a population enriched for Treg cells. Untreated cells were incubated in media alone, IL-2 was added at a concentration of $4 \times 10^{-9}$ M, and IL2/N88R/C125S/D109C and IL2/N88R/C125S/D109C-PEG samples were added at a concentration of $4 \times 10^{-8}$ M, and PEG-treated samples were incubated in a mock-PEGylation reaction containing the same amount of PEG as IL2/N88R/C125S/D109C-PEG. IL-2 stimulates a massive amount of STAT5 phosphorylation in both $CD25^{low/-}$ and $CD25^{high}$ cells. Both IL2/N88R/C125S/D109C and IL2/N88R/C125S/D109C-PEG have a qualitatively and quantitatively different effect, stimulating STAT5 phosphorylation primarily in less than 1% of the cells and primarily in $CD25^{high}$ cells.

SUMMARY OF THE INVENTION

The invention described herein is a novel IL-2 protein with selective agonist activity for Regulatory T cells and with an additional amino acid substitution that enable chemical conjugation with Polyethyene Glycol (PEG) that increase circulating half-life compared to the IL-2 selective agonist alone. Substituted amino acid positions were selected based on their exposure to solvent within the IL-2-IL2Rαβγ receptor complex and the predicted ability of the polymer-conjugated variants to retain the ability to bind to and activate the IL2Rαβγ receptor complex. A series of recombinant IL-2 variants were constructed in which cysteine amino acid residues were introduced into selected amino acid positions and ther variant proteins screened for activity. IL-2 variants that were successfully expressed and purified were refolded, conjugated to malemido-PEG polymers, and then tested for selective agonist activity on Regulatory T cells. A preferred IL-2 selective agonist variant, IL2/N88R/C125S/D109C, has thus been identified. This novel protein and its PEG conjugate will selectively and efficiently boost the levels and the activity of Regulatory T cells in patients, suppress autoimmune pathology, and will thus be a safe and effective therapeutic for the treatment of autoimmune diseases.

The invention also provides IL-2 variant proteins having at least 95% to 98% and to 100% sequence identity to Seq. ID No. 1, containing the substitution D109C and having the ability to activate T cells. The proteins of this invention may be linked to a polyethylene glycol moiety linked to the cysteine at position 109. The polyethylene glycol moiety will optionally have a molecular weight of between 5 and 40 kDa. The IL-2 variant protein of this invention may contains at least one of the substitutions selected from the group consisting of: N88R, N88I, N88G, D20H, Q126L, and Q126F. Further the IL-2 variant proteins of this invention may optionally comprise the substitution C125S. More preferable is the IL-2 variant protein in which the IL-2 protein sequence contains the substitution N88R and the substitution C125S. The proteins of this invention are optionally provided in a pharmaceutical compositions comprising the proteins of this invention and a pharmaceutically acceptable carrier.

The invention further provides for methods of increasing the circulating half life of a human IL-2 variant protein of this invention where the method comprises linking of a polyethylene glycol moiety to the cysteine residue at position 109 wherein the polyethylene glycol moiety is a of a length sufficient to increase the circulating half live of the protein compared to the same protein without the polyethylene glycol moiety. The methods of this invention further provide for the administration of the protein variants at a therapeutically effective dose sufficient to stimulate human regulatory T cell levels.

DETAILED DESCRIPTION OF THE INVENTION

Introduction

This invention is a novel IL-2 variant protein that comprises an amino acid substitution that enables specific and efficient chemical conjugation of a PEG polymer to the IL-2 variant protein while maintaining high affinity for the IL-2 receptor, high bioactivity, and an extended circulating half life compared to IL-2 itself. This variant protein was discovered through a process in which candidate amino acid positions in the IL-2 sequence that were exposed to solvent in the published IL-2-IL2Rαβγ receptor complex crystal structure were identified, and variant proteins were constructed in which cysteine residues were substituted at the selected positions. These IL-2 variants were expressed and purified, the variant proteins produced in sufficiently high levels were conjugated with PEG-malelimide, and IL2/N88R/D109C-PEG was then tested for bioactivity on Treg cells and shown to be active. The molecule defined by this invention will enable the safe and effective treatment of autoimmune diseases by the novel mechanism of stimulating the production of a small subpopulation of T cells that suppress autoimmune and inflammatory pathology. This paradigm-breaking therapeutic can potentially treat a number of different autoimmune diseases.

Definitions

When referring to variants from a wild type protein, references to amino acid substitutions such as "D109C" refer to the original residue aspartic acid (D) at position by number (109) followed by the substituted residuce cysteine (C).

"At least a percent (eg. 97%) sequence identify to Sequence ID No. 1" as used herein refers to the extent to which the sequence of two or more nucleic acids or polypeptides is the same. The percent identity between a sequence of interest and a second sequence over a window of evaluation, e.g., over the length of the sequence of interest, may be computed by aligning the sequences, determining the number of residues (nucleotides or amino acids) within the window of evaluation that are opposite an identical residue allowing the introduction of gaps to maximize identity, dividing by the total number of residues of the sequence of interest or the second sequence (whichever is greater) that fall within the window, and multiplying by 100. When computing the number of identical residues needed to achieve a particular percent identity, fractions are to be rounded to the nearest whole number. Percent identity can be calculated with the use of a variety of computer programs. For example, computer programs such as BLAST2, BLASTN, BLASTP, Gapped BLAST, etc., generate alignments and provide percent identity between sequences of interest. The algorithm of Karlin and Altschul (Karlin and Altschul, Proc. Natl. Acad. ScL USA 87:22264-2268, 1990) modified as in Karlin and Altschul, Proc. Natl. Acad. ScL USA 90:5873-5877, 1993 is incorporated into the NBLAST and XBLAST programs of Altschul et al. (Altschul, et al., J. Mol. Biol. 215:403-410, 1990). To obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. A PAM250 or BLOSUM62 matrix may be used. Software for performing BLAST analyses is publicly available through the National Center for Biotechnology Information (NCBI). See the Web site having URL world-wide web address of: "ncbi.nlm.nih.gov" for these programs. In the specific embodiment of the claims, percent identity is calculated using BLAST2 with default parameters as provided by the NCBI.

An "IL-2 Selective Agonist" of this invention is a IL-2αβγ Selective Agonist. Functionally it selectively activates the IL2Rαβγ receptor complex relative to the IL2Rβγ receptor complex. It is derived from a wild type IL-2 protein structurally defined as having at least a 95% sequence identity to the wild type IL-2 of Sequence ID No. 1 and functionally defined by the ability to preferentially activate Treg cells. The protein can also be functionally defined by its ability to selectively activate IL-2 receptor signaling in Tregs, as measured by the levels of phosphorylated STAT5 protein in Treg cells compared to CD4+ CD25−/low T cells or NK cells, or by the selective activation of Phytohemagglutinin-stimulated T cells versus NK cells.

"Tregs" or "Treg cells" refer to Regulatory T cells. Regulatory T cells are a class of T cells that suppress the activity of other immune cells, and are defined using flow cytometry by the cell marker phenotype CD4+CD25+ FOXP3+. Because FOXP3 is an intracellular protein and requires cell fixation and permeablization for staining, the cell surface phenotype CD4+CD25+CD127− can be used for defining live Tregs. Tregs also include various Treg subclasses, such as tTregs (thymus-derived) and pTregs (peripherally-derived, differentiated from naïve T cells in the periphery). All Tregs express the IL2Rαβγ receptor, do not produce their own IL-2 and are dependent on IL-2 for growth, and someone skilled in the art will recognize that both classes will be selectively activated by a IL2Rαβγ selective agonist.

A "PEG" is a poly(ethylene glycol) molecule which is a water-soluble polymer of ethylene glycol. PEG molecules can be chemically conjugated to proteins to increase their circulating half-life. PEGs can be obtained in different sizes, and can also be obtained commercially in chemically activated forms that are derivatized with chemically reactive groups to enable covalent conjugation to proteins. Activated PEGs can be obtained from commercial sources such as NOF America (White Plains, N.Y.) and Celares GmbH (Berlin, Germany). Linear PEGs are produced in various molecular weights, such as PEG polymers of weight-average molecular weights of 5,000 daltons, 10,000 daltons, 20,000 daltons, 30,000 daltons, and 40,000 daltons. Branched PEG polymers have also been developed. Commonly-used activated PEG polymers are those derivatized with N-hydroxysuccinimide groups (for conjugation to primary amines such as lysine residues and protein N-termini), with aldehyde groups (for conjugation to N-termini), and with maleimide or iodoacetamide groups (for coupling to thiols such as cysteine residues).

An "IL-2-PEG conjugate" is an IL-2 protein to which PEG has been covalently conjugated. The IL-2 moiety can be wild-type IL-2, IL-2 with a C125S substitution, one of the preceding proteins with a substitutions at N88, D20, or Q126 that results in selectivity toward the IL2Rαβγ receptor, or one of the preceding proteins with an additional substitution that enables site-specific conjugation of a PEG molecule.

"Bioactivity" refers to the measurement of biological activity in a quantitative cell-based in vitro assay.

"Functional activation of Treg cells" is defined an IL-2-mediated response in Tregs. Assay readouts for functional activation of Treg cells includes stimulation of pSTAT5, Treg cell proliferation, and stimulation of the levels of Treg effector proteins.

Design and Construction of IL-2 Moieties for Peg Conjugation

The following considerations guided the design of the IL-2 moiety that would best fulfill the desired requirements.

(1) Free (unpaired) cysteine residues were engineered into IL-2 because of the very specific reactivity of thiols with malemide- and iodoacetimide-activated PEG reagents.
(2) All constructs were made on the background of wild-type human IL-2 with the substitution C125S, to remove the only unpaired cysteine residue in IL-2, and the substitution N88R, which reduces affinity for IL2RB and thus selective for IL2Rabg. C125 is directly adjacent to the Q126, a major contact with IL2RG.
(3) Single additional cysteine substitutions were generated at surface-exposed sites on IL-2 to enable efficient conjugation with water-soluble PEG.
(4) PEG conjugation sites were also chosen such that were exposed to solvent within the IL2-IL2Rαβγ receptor complex (Wang, X., et al., 2005 Science. 310:1159-63), and thus unlikely to impair binding and activation of the IL2Rαβγ.
(5) The variant proteins must express well and fold properly. The presence of a novel free cysteine can result in improper intramolecular disulfide formation and misfolding, or intermolecular disulfide bridges with other molecules leading to aggregation.

General Methods

In general, preparation of the variant IL-2 proteins of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the fusion molecules can be isolated and purified using chaotropic agents and well known electrophoretic, centrifugation and chromatographic methods. See generally, Sambrook et al., Molecular Cloning: A Laboratory Manual (2nd ed. (1989); and Ausubel et al., Current Protocols in Molecular Biology, John Wiley & Sons, New York (1989) for disclosure relating to these methods.

The genes encoding the variant proteins of this invention involve restriction enzyme digestion and ligation as the basic steps employed to yield DNA encoding the desired fusions. The ends of the DNA fragment may require modification prior to ligation, and this may be accomplished by filling in overhangs, deleting terminal portions of the fragment(s) with nucleases (e.g., ExoIII), site directed mutagenesis, or by adding new base pairs by PCR. Polylinkers and adaptors may be employed to facilitate joining of selected fragments. The expression construct is typically assembled in stages employing rounds of restriction, ligation, and transformation of *E. coli*. Numerous cloning vectors suitable for construction of the expression construct are known in the art (lambda.ZAP, Agilent; pET, EMD Millipore) and the particular choice is not critical to the invention. The selection of cloning vector will be influenced by the gene transfer system selected for introduction of the expression construct into the host cell. At the end of each stage, the resulting construct may be analyzed by restriction, DNA sequence, hybridization and PCR analyses.

Site-directed mutagenesis is typically used to introduce specific mutations into the genes encoding the IL-2 variant proteins of this invention by methods known in the art. See, for example, U.S. Patent Application Publication 2004/0171154; Storici et al., 2001, Nature Biotechnology 19: 773-776; Kren et al., 1998, Nat. Med. 4: 285-290; and Calissano and Macino, 1996, Fungal Genet. Newslett. 43: 15-16. Any site-directed mutagenesis procedure can be used in the present invention. There are many commercial kits available that can be used to prepare the variants of this invention.

Various promoters (transcriptional initiation regulatory region) may be used according to the invention. The selection of the appropriate promoter is dependent upon the proposed expression host. Promoters from heterologous sources may be used as long as they are functional in the chosen host.

IL-2 proteins may be expressed in *E. coli* without a signal sequence, and proteins recovered from inclusion bodies and refolded into active form. Such an expression system described in U.S. Pat. No. 7,105,653 B2.

Various signal sequences may be used to facilitate expression of the proteins described herein. Signal sequence are selected or designed for efficient secretion and processing in the expression host may also be used. The native human IL-2 signal sequence, the signal sequence which is homologous to the TCR coding sequence, or the signal sequence which is homologous to the mouse IL-2 coding sequence may be used for mammalian cells. Other suitable signal sequence/host cell pairs include the *B. subtilis* sacB signal sequence for secretion in *B. subtilis*, and the *Saccharomyces cerevisiae* α-mating factor or *P. pastoris* acid phosphatase phoI signal sequences for *P. pastoris* secretion. The signal sequence may be joined directly through the sequence encoding the signal peptidase cleavage site to the protein coding sequence, or through a short nucleotide bridge.

Elements for enhancing transcription and translation have been identified for eukaryotic protein expression systems. For example, positioning the cauliflower mosaic virus (CaMV) promoter 1000 bp on either side of a heterologous promoter may elevate transcriptional levels by 10- to 400-fold in plant cells. The expression construct should also include the appropriate translational initiation sequences. Modification of the expression construct to include a Kozak consensus sequence for proper translational initiation may increase the level of translation by 10 fold.

The expression cassettes are joined to appropriate vectors compatible with the host that is being employed. The vector must be able to accommodate the DNA sequence coding for the fusion proteins to be expressed. Suitable host cells include eukaryotic and prokaryotic cells, preferably those cells that can be easily transformed and exhibit rapid growth in culture medium. Specifically preferred hosts cells include prokaryotes such as *E. coli, Bacillus subtillus*, etc. and eukaryotes such as animal cells and yeast strains, e.g., *S. cerevisiae*. Mammalian cells are generally preferred, particularly HEK, J558, NSO, SP2-O or CHO. Other suitable hosts include, e.g., insect cells such as Sf9. Conventional culturing conditions are employed. See Sambrook, supra. Stable transformed or transfected cell lines can then be selected. In vitro transcription-translation systems can also be employed as an expression system.

Nucleic acid encoding a desired IL-2 variant protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et al. supra, and other laboratory textbooks.

Alternatively, one can use synthetic gene construction for all or part of the construction of the proteins described herein. This entails in vitro synthesis of a designed polynucleotide molecule to encode a polypeptide molecule of interest. Gene synthesis can be performed utilizing a number of techniques, such as the multiplex microchip-based technology described by Tian, et. al., (Tian, et. al., Nature 432:1050-1054) and similar technologies wherein olgionucleotides are synthesized and assembled upon photo-programmable microfluidic chips.

The IL-2 variant proteins of this invention are isolated from harvested host cells or from the culture medium. Standard protein purification techniques are used to isolate the proteins of interest from the medium or from the harvested cells. In particular, the purification techniques can be used to express and purify a desired IL-2 variant protein on a large-scale (i.e., in at least milligram quantities) from a variety of approaches including roller bottles, spinner flasks, tissue culture plates, bioreactor, or a fermenter.

Protein expression systems have been developed that enable incorporation of non-natural amino acids into recombinant proteins (Kim, C. H., et al. Curr Opin Chem Biol. 2013 S1367-5931(13)00071-9). These expression systems can incorporate non-natural amino acids that have chemical reactivity that enables site-specific PEGylation of proteins at those positions. As an alternative to the use of free cysteine residues, someone skilled in the art would recognize that the IL-2 amino acid positions identified herein could also be substituted with non-natural amino acids instead of cysteine to accomplish similar goals of attaching PEG or other non-immunogenic polymers to IL-2 for the purpose of increasing circulating half-life.

A skilled artisan would also recognize that the IL2 selective agonist moiety of this invention could also be conjugated with other non-immunogenic polymers. Two such polymers are recombinant non-immunogenic amino acid polymers such as XTEN polymers, chains of A, E, G, P, S, and T amino acids (Schellenberger, V., et. al., 2009, Nat Biotechnol. 27:1186-90)), and PAS polymers, chains of P, A, and S amino acid residues (Schlapschy, M., et. al., 2007, Protein Eng Des Sel. 20:273-84).

The IL2 Selective Agonist Moiety

IL-2 with the substitution N88R is an exemplary case of an IL2 Selective Agonist for the IL2Rαβγ receptor (Shanafelt, A. B., et al., 2000, Nat Biotechnol. 18:1197-202). IL2/N88R is deficient in binding to the IL2RB receptor subunit and the IL2Rβγ receptor complex, but is able to bind to the IL2Rαβγ receptor complex and stimulate the proliferation of IL2Rαβγ-expressing PHA-activated T cells as effectively as wt IL-2, while exhibiting a 3,000 fold reduced ability to stimulate the proliferation of IL2Rβγ-expressing NK cells, Other IL2Rαβγ selective agonists with similar activity profiles include IL-2 with the substitutions N88I, N88G, and D20H, and other IL2 variants with the substitutions Q126L and Q126F (contact residues with the IL2RG subunit) also possess IL2Rαβγ-selective agonist activity (Cassell, D. J., et. al., 2002, Curr Pharm Des., 8:2171-83). A practitioner skilled in the art would recognize that any of these IL2 Selective Agonist molecules can be substituted for the IL2/N88R moiety with the expectation that an Fc fusion protein will have similar activity. All of the aforementioned mutations can be made on the background of wt IL-2, or wt IL-2 with the substitution C125S, which is a substitution that promotes IL-2 stability by eliminating an unpaired cysteine residue. This invention can also be used with other mutations or truncations that improve production or stability without significantly impacting IL-2 receptor activating activity.

The variants of this invention optionally include conservatively substituted variants that apply to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations, which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

With regard to conservative substitution of amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a conservatively modified variant where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W).

Examples of conservative substitutions that would be tolerated in IL-2 include Y, 31F, T51S, Q57N, E100D, and T111S.

Bioassays

Robust and quantitative bioassays are necessary for the characterization of the biological activity of candidate proteins. These assays should measure the activation of the IL2 receptor, measure the downstream functional consequences of activation in Tregs, and measure therapeutically-relevant outcomes and functions of the activated Tregs. These assays can be used the measure the therapeutic activity and potency of IL2 PEG conjugate molecules, and can also be used for measurement of the pharmacodynamics of an IL2 PEG conjugate in animals or in humans. One assay measures the phosphorylation of the signal transduction protein STAT5, measured flow cytometry with an antibody specific for the phosphorylated protein (pSTAT5). Phosphorylation of STAT5 is an essential step in the IL-2 signal transduction pathway. STAT5 is essential for Treg development, and a constitutively activated form of STAT5 expressed in CD4+ CD25+ cells is sufficient for the production of Treg cells in the absence of IL-2 (Mahmud. S. A., et al., 2013, JAKSTAT 2:e23154). Therefore, measurement of phosphorylated STAT5 (pSTAT5) in Treg cells will be recognized by someone skilled in the art as reflective of IL-2 activation in these cells, and will be predictive of other biological outcomes of IL-2 treatment given appropriate exposure time and conditions. Another assay for functional activation measures IL-2-stimulated proliferation of Treg cells. Someone skilled in the art will recognize that Treg proliferation can be measured by tritiated thymidine incorporation into purified Treg cells, by an increase in Treg cell numbers in a mixed population of cells measured by flow cytometry and the frequencies of CD4+CD25+FOXP3+ or the CD4+CD25+ CD127− marker phenotypes, by increased expression in Treg cells of proliferation-associated cell cycle proteins, such as Ki-67, or by measurement of the cell division-associated dilution of a vital fluorescent dye such as carboxyfluorescein succinimidyl ester (CFSE) by flow cytometry in Treg cells. Another assay for functional activation of Tregs with IL-2 is the increased stability of Tregs. pTreg cells are thought by some to be unstable, and have the potential to differentiate into Th1 and Th17 effector T cells. IL-2 activation of Tregs can stabilize Tregs and prevent this differentiation (Chen, Q., et al., 2011, J Immunol. 186:6329-37). Another outcome of IL-2 stimulation of Tregs is the stimulation of the level of Treg functional effector molecules, such as CTLA4, GITR, LAG3, TIGIT, IL-10, CD39, and CD73, which contribute to the immunosuppressive activity of Tregs.

Formulation

Pharmaceutical compositions of the fusion proteins of the present invention are defined as formulated for parenteral (particularly intravenous or subcutaneous) delivery according to conventional methods. In general, pharmaceutical formulations will include fusion proteins of the present invention in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in Remington: The Science and Practice of Pharmacy, Gennaro, ed., Mack Publishing Co., Easton, Pa., 19.sup.th ed., 1995.

As an illustration, pharmaceutical formulations may be supplied as a kit comprising a container that comprises fusion proteins of the present invention. Therapeutic proteins can be provided in the form of an injectable solution for single or multiple doses, as a sterile powder that will be reconstituted before injection, or as a prefilled syringe. Such a kit may further comprise written information on indications and usage of the pharmaceutical composition. Moreover, such information may include a statement that the fusion proteins of the present invention is contraindicated in patients with known hypersensitivity to fusion proteins of the present invention.

The IL-2-PEG conjugate of this invention can be incorporated into compositions, including pharmaceutical compositions. Such compositions typically include the protein and a pharmaceutically acceptable carrier. As used herein, the term "pharmaceutically acceptable carrier" includes, but is not limited to, saline, solvents, dispersion media, coatings, antibacterial and antifungal agents, isotonic and absorption delaying agents, and the like, compatible with pharmaceutical administration. Supplementary active compounds (e.g., antibiotics) can also be incorporated into the compositions.

A pharmaceutical composition is formulated to be compatible with its intended route of administration. The IL-2-PEG conjugate of the invention is likely that to be administered through a parenteral route. Examples of parenteral routes of administration include, for example, intravenous, intradermal, and subcutaneous. Solutions or suspensions used for parenteral application can include the following components: a sterile diluent such as water for injection, saline solution, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5). The parenteral preparation can be enclosed in ampoules, disposable syringes or multiple dose vials made of glass or plastic.

Pharmaceutical compositions suitable for injectable use include sterile aqueous solutions or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition should be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The maintenance of the required particle size in the case of dispersion may be facilitated by the use of surfactants, e.g., Polysorbate or Tween. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the IL-2-PEG conjugate is prepared with carriers that will protect the IL-2-PEG conjugate against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques.

The pharmaceutical compositions can be included in a container, pack, or dispenser together with instructions for administration.

Administration

IL-2-PEG conjugates of the present invention will preferably be administered by the parenteral route. The subcutaneous route is the preferred route, but intravenous, intramuscular, and subdermal administration can also be used. For subcutaneous or intramuscular routes, depots and depot formulations can be used. For certain diseases specialized routes of administration can be used. For instance, for inflammatory eye diseases intraocular injection can be used. Fusion proteins can be used in a concentration of about 0.1 to 10 mcg/ml of total volume, although concentrations in the range of 0.01 mcg/ml to 100 mcg/ml may be used.

Determination of dose is within the level of ordinary skill in the art. Dosing is daily or weekly over the period of treatment, or may be at another intermittent frequency. Intravenous administration will be by bolus injection or infusion over a typical period of one to several hours. Sustained release formulations can also be employed. In general, a therapeutically effective amount of the IL-2-PEG conjugate of the present invention is an amount sufficient to produce a clinically significant change in the treated condition, such as a clinically significant change in circulating Treg cells, a clinically significant change in Treg cells present within a diseased tissue, or a clinically significant change in a disease symptom.

The data obtained from the cell culture assays and animal studies can be used in formulating a range of dosage for use in humans. The dosage of such compounds lies preferably within a range of circulating concentrations that include the half maximal effective concentration (EC50; i.e., the concentration of the test compound which achieves a half-maximal stimulation of Treg cells) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the EC50 as determined in cell culture. Such information can be used to more accurately determine useful doses in humans. Levels in plasma may be measured, for example, by enzyme-linked immunosorbent assays.

As defined herein, a therapeutically effective amount of a IL-2-PEG conjugate (i.e., an effective dosage) depends on the polypeptide selected and the dose frequency. For instance, single dose amounts in the range of approximately 0.001 to 0.1 mg/kg of patient body weight can be administered; in some embodiments, about 0.005, 0.01, 0.05 mg/kg may be administered. The compositions can be administered from one time per day to one or more times per week, or one or more times per month; including once every other day. The skilled artisan will appreciate that certain factors may influence the dosage and timing required to effectively treat a subject, including but not limited to the severity of the disease or disorder, previous treatments, the general health and/or age of the subject, the level of Treg cells present in the patient, and other diseases present. Moreover, treatment of a subject with a therapeutically effective amount of the IL-2 selective agonist PEG conjugate of the invention is likely to be a series of treatments.

Autoimmune Diseases

Some of the diseases that can benefit from the therapy of this invention have been noted. However, the role of Treg cells in autoimmune diseases is a very active area of research, and additional diseases will likely be identified as treatable by this invention. Autoimmune diseases are defined as human diseases in which the immune system attacks its own proteins, cells, and tissues. A comprehensive listing and review of autoimmune diseases can be found in *The Autoimmune Diseases* (Rose and Mackay, 2014, Academic Press).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of noncritical parameters which could be changed or modified to yield essentially similar results.

1. Prediction of Candidate PEG Attachment Sites in IL-2

To select candidate sites for conjugating PEG to IL-2, amino acid residues that are exposed to solvent and do not appear to interfere directly or sterically with IL-2 binding to the IL-2Rαβγ were identified. The strategy is shown diagrammatically in FIG. 2. Inspection of the published crystal structure of IL-2 in complex with the extracellular domains of the IL-2Rαβγ receptor (Wang, X., et al., 2005, Science 310:1159-63, Stauber, D. J., et al., 2006, Proc Natl Acad Sci 103:2788-93) identified the following residues: S6, K8, K48, K49, T51, E52, K54, K97, G98, F103, M104, E106, D109, and T133 (FIG. 3). Additional amino acid residues that are not visible in the crystal structure, but, based on information about neighboring residues are likely to fulfill the criteria, are A1, P2, T3, S4, S5, S99, E100, T101, and T102. Based on this list of candidates, 12 variants (T3C, S6C, K8C, K48C, K49C, T51C, K97C, G98C, F103C, M104C, E106C, and D109C) with cysteine substitutions at the indicated positions were constructed and produced (TABLE 1).

2. Cloning, Expression, and Purification of IL2 Selective Agonist Variant Proteins in *E. coli.* cDNAs encoding proteins with each of the substitutions listed in Table 1 made on the background of human IL-2 (SEQ ID NO: 1) containing the substitutions N88R and C126S were prepared by DNA synthesis (Genescript, Piscataway, N.J.), incorporating the restriction sites NCOI and BAM HI at the 5' and 3' ends, respectively, and cloned into pUC57. cDNA inserts were then cloned into the pET3d vector (EMD Millipore, Billerica, Mass.) using the Nco1 and BAM H1 sites. Constructs were transformed into BL21 (DE3) cells and selected for ampicillin resistance. Transformed cells were grown in LB media containing 50 ug/ml ampicillin and 1% glucose at 37 C in 0.5 L cultures to an ABS280 of between 0.6 and 1.0. IPTG was then added to 0.5 mM to induce protein expression, and cultures harvested at 3 hours post-induction.

Cells were pelleted by centrifugation at 10,000×g for 10 minutes. Inclusion bodies (IB) were extracted and purified from cell pellets using Bugbuster (EMD Millipore, Billerica, Mass.) according to the manufacturers instructions, and a sample taken for analysis by SDS-PAGE. IBs were dissolved and denatured in 8 M guanidine hydrochloride in 0.1 M Tris/HCL (pH 8.0) containing 0.1% (vol/vol) 2-mercaptoethanol for 2 hours at room temperature. Proteins were then refolded by dialysis against 20 volumes of 10 mM Tris/HCL (pH 8.0)/1 mM EDTA for 12 hours at room temperature. Trifluoroacetic acid (TFA) was then added to the samples to 0.1%, samples clarified by centrifugation to remove precipitate, filtered through a 0.2 uM filter, and purified by reverse phase chromatography. IL-2 variants were loaded onto a Vydac 208TP54 C-8 column in 0.1% TFA at a flow rate of 1 ml/minute and were eluted with a 45 min gradient of 0-75% acetonitrile in 0.1%/TFA. Fractions were screened by SDS-PAGE, with IL-2 variant proteins typically eluting at approximately 60% acetonitrile.

The results of these production studies are summarized in TABLE 1. Of the 12 variants selected for production, only 7 yielded detectable IL-2 protein peaks after reverse-phase chromatography. Of these 7 proteins, 5 exhibited yields that were very low and produced insufficient material for further studies at the scale performed. Of the remaining 2 proteins, one, the D109C variant, which was produced at the highest level, was PEGylated and tested. These results indicate that the ability to produce these variant proteins with single unpaired cysteine residues varies widely, and that many can not be easily produced. This could be due to a variety of factors, such as toxicity of the recombinant protein to the *E. coli* host, inability to form inclusion bodies, or low efficiency of refolding. Modification of the production process, or expressing the proteins in other expression systems, such as in mammalian cells as a secreted protein, could improve productivity of some of the other variants. However, in this expression system the D109C variant exhibits clearly superior from the production levels.

TABLE I

Summary of the production of
IL-2 variant proteins in *E. coli*.

| IL-2 Selective Agonist Variant | Peak Height, mAU (280 nM) |
|---|---|
| — | 1 |
| T3C | nd |
| S6C | nd |
| K8C | nd |
| K48C | 1 |
| K49C | 11 |
| T51C | nd |
| K97C | 1 |
| G98C | 1 |
| F103C | nd |
| M104C | 2 |
| E106C | nd |
| D109C | 26 |

Peak height represents the relative final yield of variant protein on reverse phase chromatography.
nd = peak not detected.

3. PEGylation of IL2/N88R/C125S/D109C.

Purified IL2/N88R/C125S/D109C was conjugated to a 20 kDa PEG to test bioactivity of the conjugate. IL2/N88R/C125S/D109C was dialysed into 0.1 M MES (pH 6.0), protein concentration determined by OD280 using an extinction coefficient of 0.655 (Abs 280 nM at 0.1%), and reacted with a 50 fold molar excess of maleimide-PEG (20,000 g/M; NOF America, White Plains, N.Y.) for 30 minutes at room temperature. The reaction was stopped by adding L-cysteine to a 2-fold molar excess over malemide-PEG. Analysis of 10 ug of the reaction mixture by SDS-PAGE indicated no detectable residual unreacted IL-2 protein.

4. Activity of PEGylated IL2/N88R/C125S/D109C on T cells.

The activity of PEGylated IL2/N88R/C125S/D109C on T cells was determined by measuring stimulation of phospho-STAT5 (pSTAT5) levels in CD4+ T cell subsets. Activation of the IL-2 receptor, through binding of IL-2 to a heterodimer of IL2RB and IL2RG, promotes the interaction of the JAK1 and JAK3 proteins with the IL2RB and IL2RG cytoplasmic domains, respectively, stimulating the phosphorylation of the STAT5 protein (pSTAT5) that then transduces the IL-2 signal to the nucleus. STAT5 is necessary for the development of Treg cells, and artificial activation of STAT5 in CD4+ T cells is sufficient for productions of Treg cells in the absence of IL-2 (Mahmud, S. A., et al., 2013, JAKSTAT 2:e23154). Levels of pSTAT5 were measured with an antibody to a phosphorylated STAT5 peptide by fluorescent activated cell sorting (FACS) in permeabilized cells. Treg cells constitutively express CD25, and cells that are in the top 1% of CD25 expression levels are highly enriched for Treg cells (Jailwala, P., et al., 2009, PLoS One. 2009; 4:e6527; Long, S. A., et al., 2010, *Diabetes* 59:407-15). Therefore, the FACS data was gated into $CD25^{high}$ (the top 1-2% of CD25 expressing cells) and $CD25^{low/-}$ groups.

Cryopreserved human PBMC (Astarte Biologics, Seattle, Wash.) were defrosted, washed in X-VIVO 15 (Lonza, Allendale, N.J.) media containing 1% human AB serum (Mediatech, Manassas, Va.) and allowed to recover for 2 hours at 37 C. Cells were then distributed in 0.1 ml into 15×75 mm tubes at a concentration of 5×10⁶ cells/ml. Cells were treated with 4 nM IL-2, 40 nM PEG-IL2/N88R/D109C or IL2/N88R/D109C, or an equivalent amount of malemido-PEG reacted with L-cysteine for 10 minutes at 37 C, and then fixed with Cytofix Fixation Buffer at 37 C for 10 minutes. Fixed cells were permeabilized with Perm Buffer III (BD Biosciences, Santa Clara, Calif.) for 30 minutes on ice, washed, and then stained with a mixture of anti-CD4-Pacific Blue (BD Biosciences, Santa Clara, Calif.), anti-CD25-AF488 (eBioscience, San Diego, Calif.), and anti-pSTAT5-AF547 (BD Biosciences) antibodies for 30 minutes at 20 C, washed, and analyzed by FACS on an LSRII flow cytometer (BD Biosciences).

Figure 2:
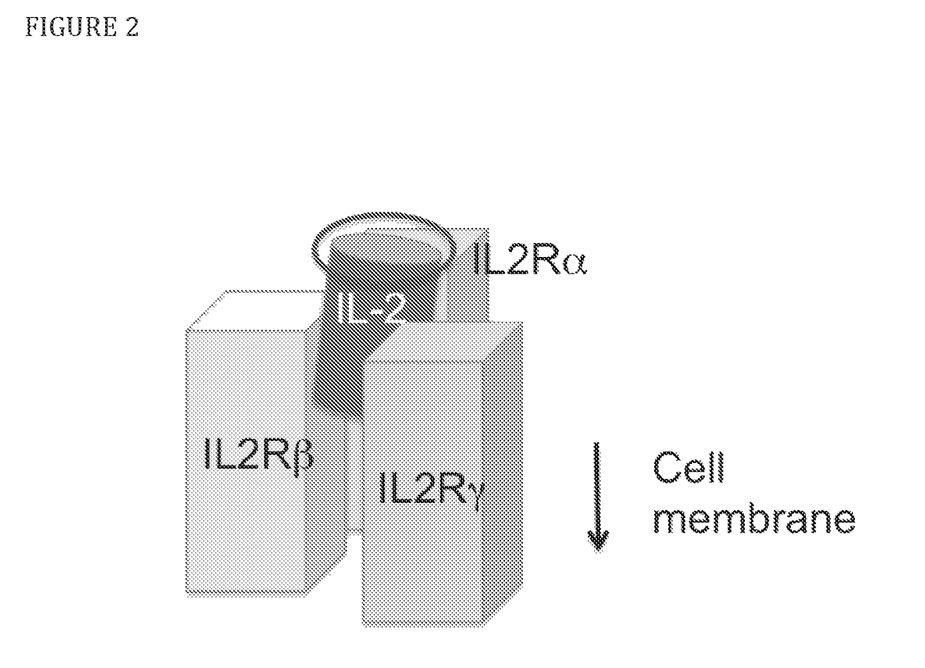
FIG. 2 represents the strategy for determining the attachment sites for PEG or other non-immunogenic polymer conjugation. IL-2 is depicted in complex with the three subunits of the high affinity IL-2 receptor. IL-2 surface amino acid residues exposed to solvent not interacting with IL-2 receptor subunits are candidate amino acid residues for attachment of PEG polymers is circled.
Figure 3:
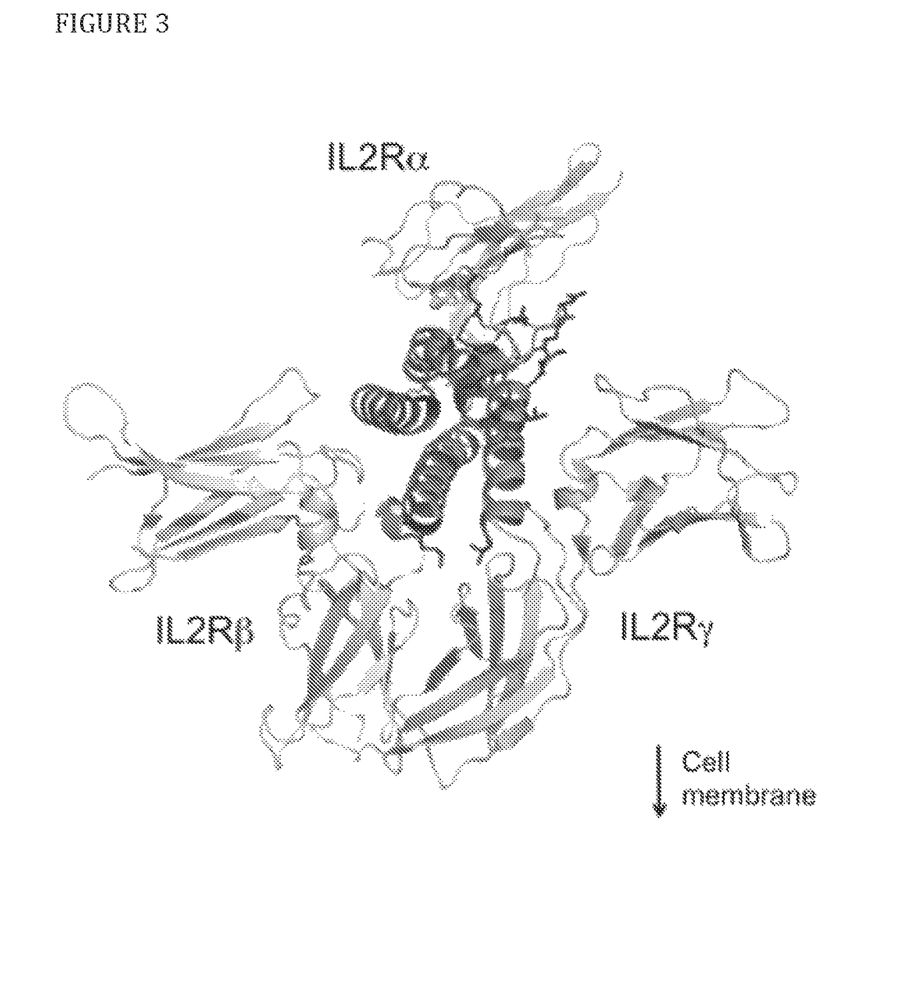
FIG. 3 shows the 3-D crystal structure of the IL-2/IL-2Rαβγ complex, indicating the amino acid side chains of the residues that fulfill criteria for attaching PEG or other non-immunogenic polymers. The residues indicated are T3C, S6C, K8C, K48C, K49C, T51C, K97C, G98C, F103C, M104C, E106C, and D109C. IL-2 is indicated the center foreground, IL-2RB on the left, IL-2RΓ on the right), and IL-2RA on the top and rear. The orientation of the receptor complex relative to the cell membrane is indicated by the arrow.
Figure 4:
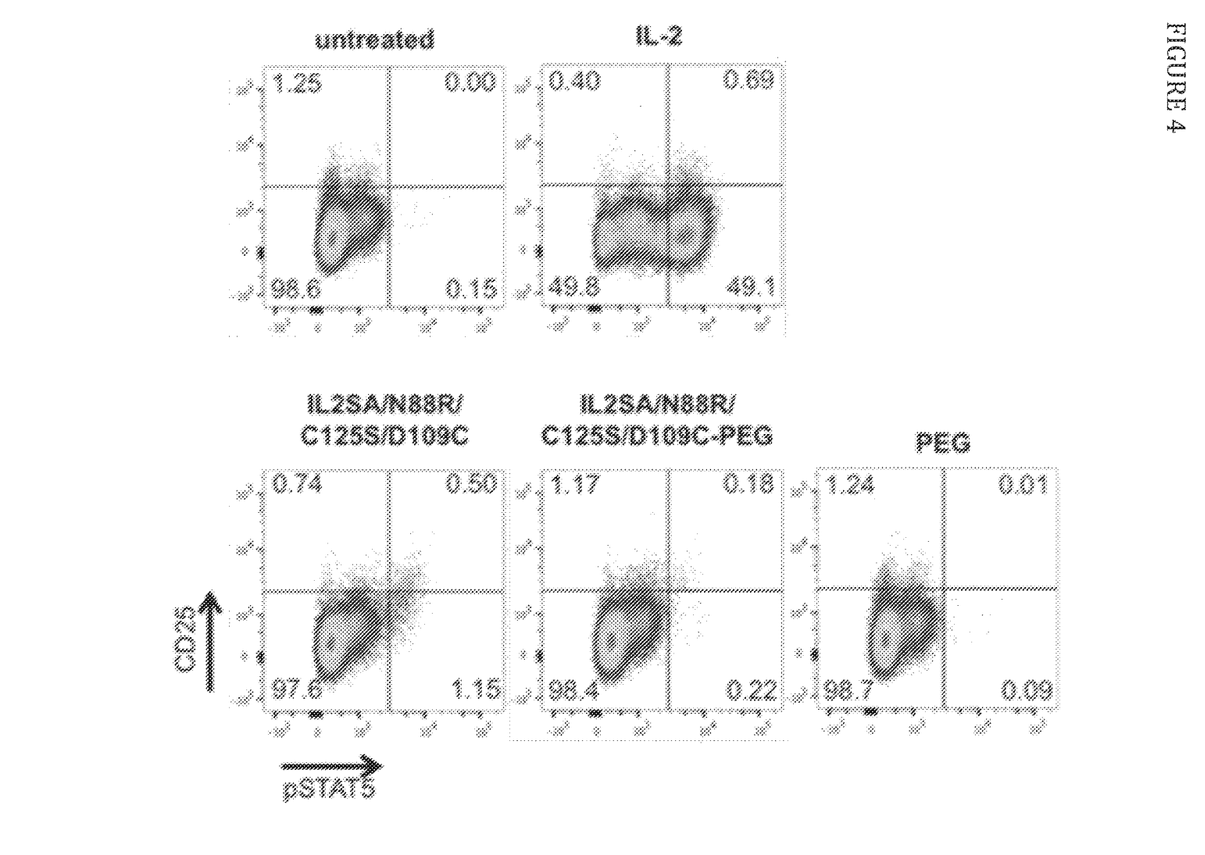

The results of this experiment indicated that both 1 L2/N88R/C125S/D109C and IL2/N88R/C125S/D109C-PEG selectively activated a small subpopulation of CD4+ $CD25^{high}$ cells enriched for Treg cells compared to IL-2 (FIG. 2). IL-2 activated over 80% of CD4+ T cells at 4 nM IL-2, with a high proportion of the activated cells expressing low levels of or no CD25. These results indicate that PEGylated IL2/N88R/C125S/D109C retains selective ability to activate Tregs.

5. Selectivity of IL2 Selective Agonist-PEG Conjugate Protein in Human PBMC

To determine the selectivity of IL2/N88R/C125S/D109C-PEG in a broader biological context, an assay was developed to measure STAT5 activation across all key immune cell types in crude unfractionated human PBMC. Human PBMC were isolated by Ficoll-Hypaque centrifugation from a normal volunteer. 10⁶ PBMC were suspended in X-VIVO15 media with glucose (Lonza) and 10% FBS (Omega), and were treated with $10^{-8}$ M test proteins for 20 min at 37° C. Cells were then treated with Foxp3/Transcription Factor Staining Buffer Set (EBIO) according to the manufacturer's instructions. Cells were then fixed with Cytofix buffer and permeabilized with Perm Buffer III as described in Example 3. Fixed and permeabilized cells were then washed with 1% FBS/PBS and stained with antibody mixture for 60 minutes at room temperature in the dark. Stained cells were then washed in 1% FBS/PBS, resuspended in PBS, and analyzed on a Fortessa flow cytometer (BD Biosciences). The antibody mix consisted of: anti-CD4-PerCP-Cy5.5 (BD, #560650), anti-pSTAT5-AF-488 (BD, #612598), anti-CD25-PE (BD. #560989), anti-CD56-PE-CF594 (BD, #562328), anti-FOXP3-AF647 (BD, #560889), anti-CD3-V450 (BD, 560366), and anti-CD8-BV650 (Biolegend, #301041). This staining procedure enabled monitoring of pSTAT5 levels in 7 key immune cells types.

Cell phenotypes were defined as follows: Treg cells: CD3+, CD4+, Foxp3+, $CD2^{high}$, CD8−, CD56−; activated CD4 Teff cells: CD3+, CD4+, Foxp3−, $CD25^{high}$, CD8−, CD56−; CD4 Teff cells: CD3+, CD4+, Foxp3−, $CD25^{low}$, CD8−, CD56−; NKT cells: CD3+, CD4−, Foxp3−, $CD25^{low}$, CD8−, CD56+; NK cells: CD3−, CD4−, Foxp3−, $CD25^{low}$, CD8−, CD56+; B cells: CD3−, CD4−, Foxp3−, $CD25^{low}$, CD8−, CD56−.

Figure 5:
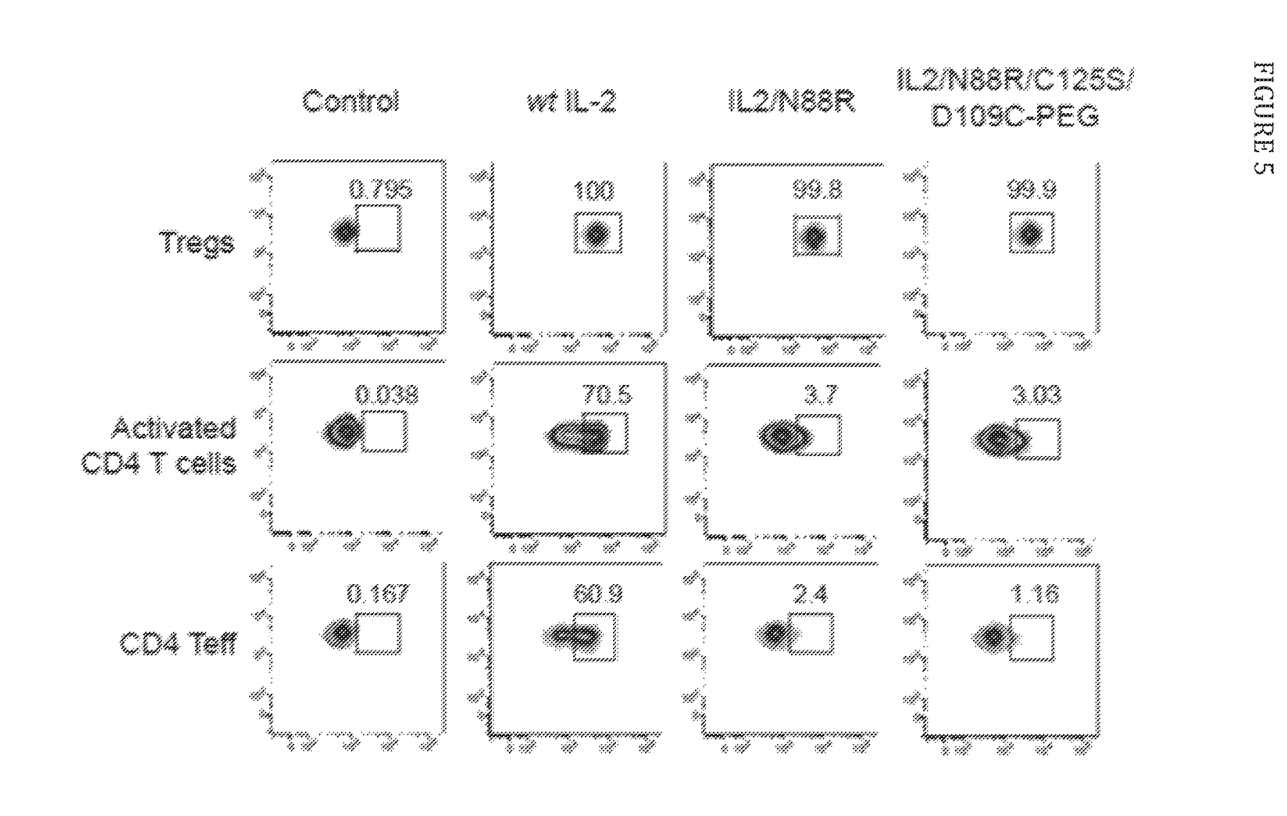
FIG. 5 demonstrates the selectivity of IL-2 and IL-2 Selective Agonist proteins on 7 different immune cell types in human PBMC. Both IL2/N88R/C125S/D109C and IL2/N88R/C125S/D109C-PEG are highly selectivity for Tregs compared to wt IL-2, and shows greater selectivity in multiple cell types than IL-2.

Proteins were tested in this assay at a concentration of $10^{-8}$ M. The results, shown in FIG. 5, show that both IL2/N88R/C125S/D109C and IL2/N88R/C125S/D109C-PEG exhibited remarkable selectivity compared to wt IL2, which activated pSTAT5 in large fractions of all the cell populations. IL2/N88R/C125S/D109C-PEG stimulated pSTAT5 signal in the Treg population at essentially the same level as that of wt IL-2. Additional analysis (not shown) showed that the pSTAT5+ NK cells were $CD25^{high}$, which is characteristic of NK-$CD56^{bright}$ cells, an NK cell subpopulation which also has immunoregulatory activity (Poli, A, et al., 2009 Immunology. 126(4):458-65). These results demonstrate the activity and high selectivity of IL2/N88R/C125S/D109C-PEG for Tregs in a complex biological milieu.

What is claimed is:

1. An IL-2 variant protein containing the substitution D109C in the amino acid sequence of SEQ ID NO: 1, wherein the IL-2 variant protein contains at least one additional substitution selected from the group consisting of: C125S, N88R, N88I, N88G, D20H, Q126L, and Q126F.

2. The IL-2 variant protein of claim 1 having a polyethylene glycol moiety linked to the cysteine at position 109, wherein the polyethylene glycol moiety has a molecular weight of between 5 and 40 kDa.

3. The IL-2 variant protein of claim 2, wherein the IL-2 variant protein contains the substitution N88R and the substitution C125S.

4. A pharmaceutical composition comprising the IL-2 variant protein of claim 1 and a pharmaceutically acceptable carrier.

5. The IL-2 variant protein of claim 1, wherein the IL-2 variant protein contains the substitution N88R and the substitution C125S.

* * * * *